United States Patent [19]
Zimmerman et al.

[11] Patent Number: 5,952,323
[45] Date of Patent: Sep. 14, 1999

[54] CARBAPENEM ANTIBIOTIC

[75] Inventors: Jeffrey A. Zimmerman, Chalfont, Pa.; John M. Williams, Belle Mead, N.J.; Paul A. Bergquist, Collegeville, Pa.; Lisa M. DiMichele, Berkeley Heights, N.J.; David C. DuBost, Collegeville; Michael J. Kaufman, New Hope, both of Pa.; Daniel R. Sidler, Whitehouse Station, N.J.; William A. Hunke, Harleysville, Pa.

[73] Assignee: Merck & Co., Inc., Rahway, N.J.

[21] Appl. No.: 09/064,426

[22] Filed: Apr. 22, 1998

Related U.S. Application Data

[62] Division of application No. 08/856,560, May 15, 1997, abandoned.

[51] Int. Cl.$^6$ .......... A61K 31/40; C07D 207/16; C07D 403/12; C07D 477/20
[52] U.S. Cl. .......... 514/210; 540/200; 540/350; 548/413; 548/537
[58] Field of Search .......... 514/210; 540/200, 540/350; 548/413, 537

[56] References Cited

U.S. PATENT DOCUMENTS 5,478,820  12/1995  Betts et al. .
5,652,233  7/1997  Betts et al. .

FOREIGN PATENT DOCUMENTS

WO 93/15078  2/1992  WIPO .

OTHER PUBLICATIONS

Betts, et al., *Chem Abs.*, 118:80721, 1992.

*Primary Examiner*—Zohreh Fay
*Attorney, Agent, or Firm*—James M. Hunter, Jr.; Sylvia A. Ayler; Mark R. Daniel

[57] ABSTRACT

A pharmaceutical composition is disclosed which contains a compound of formula I:

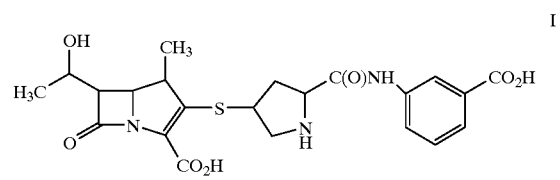

or a pharmaceutically acceptable salt, prodrug or hydrate thereof, in the stabilized form and/or in combination with a carbon dioxide source.

6 Claims, No Drawings

CARBAPENEM ANTIBIOTIC

This application is a division of application Ser. No. 08/856,560 filed on May 15, 1997. Now abandoned.

BACKGROUND OF THE INVENTION

The present invention relates to a carbapenem antibiotic composition, a stabilized form of the antibiotic and methods of preparation thereof. The composition can be used in the treatment of infectious diseases, including gram positive and negative, aerobic and anaerobic bacteria. The composition provides good stability against beta-lactamases, and a favorable duration of action.

SUMMARY OF THE INVENTION

A pharmaceutical composition is disclosed which contains a compound of formula I:

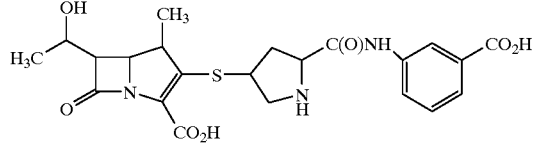

or a pharmaceutically acceptable salt, stabilized form, prodrug or hydrate thereof in combination with a carbon dioxide source.

DETAILED DESCRIPTION OF THE INVENTION

As used herein, the term "stabilized form" refers to compounds which have a carbamate group formed at the pyrrolidine nitrogen atom, as shown in compounds of formula II. This carbamate is obtainable by combining a compound of formula I or a salt, prodrug or hydrate thereof with a carbon dioxide source, such as sodium carbonate or sodium bicarbonate. Examples are shown as formula II and II-a through II-g.

The term "pro-drug" refers to compounds with a removable group attached to the hydroxyl of the hydroxyethyl side chain (position 6 of the carbapenem nucleus), the carboxylic acid at position 3 of the carbapenem nucleus or the meta-carboxylic acid group on the phenyl ring of the side chain. Groups which are useful in forming pro-drugs should be apparent to the medicinal chemist from the teachings herein. Examples include allyl, acetyl, benzyloxycarbonyl, methoxymethyl, t-butoxycarbonyl, trimethylsilyl and the like.

The term "hydrate" is used in the conventional sense to include the compounds of formula I and II in physical association with water.

The present invention relates to pharmaceutical compositions which contain the carbapenem antibiotic compound:

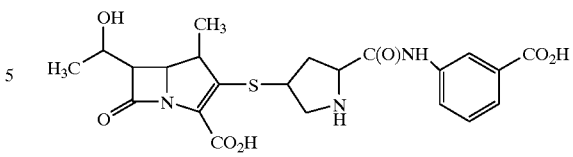

as well as salts, stabilized forms, prodrugs and hydrates thereof. Compound I is a carbapenem antibiotic that is particularly useful for intravenous and intramuscular administration.

In one aspect of the invention, the pharmaceutical composition is formulated with any pharmaceutically acceptable buffer which will provide a pH of about 6.0 to about 9.0 upon dissolution. For example, sodium bicarbonate is a preferred pharmaceutically acceptable buffer. Preferably the pH of the composition upon dissolution is about 6.2 to about 8.5.

In another aspect of the invention, a stabilized form of the compound, shown below as formula I, is included. Generally, any compound which provides carbon dioxide upon dissolution can be used with a compound of formula I to form a compound of formula II.

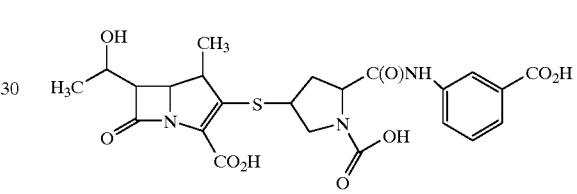

The compositions of the present invention are generally formulated using a carbon dioxide source. Preferred sources of carbon dioxide are carbon dioxide (gas, liquid or solid), carbonates and bicarbonates, and more preferably sodium carbonate and sodium bicarbonate, which can be incorporated into the formulation, such that an appropriate pH, e.g., about 6.2–8.5, is obtained upon dissolution. The native pH of the monosodium salt of compound I is approximately 5.4.

Compounds of formula I can be synthesized in accordance with U.S. Pat. No. 5,478,820 issued to Betts, et al. on Dec. 26, 1995, the teachings of which are incorporated herein by reference. The compound of formula I in lyophilized or non-lyophilized form, combined with the compound which produces carbon dioxide, such as sodium carbonate or sodium bicarbonate, is converted to a compound of formula II.

Generally compounds of formula II can be synthesized by combining a compound of formula I with the carbon dioxide source, and then dissolving the blend in an appropriate solvent. The compound of formula I can be blended with the carbon dioxide source, and the blend dissolved, which generally produces the compound of formula II.

In many instances it is preferred to dissolve the compound of formula I with the carbon dioxide producing compound, in an aqueous solvent, and then to lyophilize the resulting composition, thus providing a mixture containing compounds of formula II.

Upon dissolution, the compound of formula II (II, and II-a through II-g) converts into a compound of formula I (I, I-a, I-b and I-c) over time.

The compound of formula I can be powder blended with a carbon dioxide producing compound, such that the compound of formula II, or the salt, prodrug or hydrate thereof, is produced upon dissolution or reconstitution.

Alternatively, the compound of formula I and the carbon dioxide producing compound can be combined in solution to form compound II, after which the composition is lyophilized to provide a composition containing a compound of formula II, or a salt, prodrug or hydrate thereof.

The amount of sodium carbonate or sodium bicarbonate used in the composition can be varied within wide limits. For example, the amount of sodium carbonate in the formulation can be varied from as low as about 0.025 g of sodium carbonate/gram of drug to as high as about 0.25 g of sodium carbonate/gram of drug. Likewise, the amount of sodium bicarbonate in the formulation can be varied from as low as about 0.025 g/gram of drug, to as high as about 0.7 g/gram of drug. Other compounds can be included to adjust the pH of the composition upon dilution or reconstitution. Examples include potassium hydroxide, sodium hydroxide, N-methyl glucamine and the like.

One formulation that is of particular interest is comprised of about 3–6 parts by weight, and preferably about 4.5 parts by weight, of compound I, or the pharmaceutically acceptable salt, stabilized form, prodrug or hydrate thereof, and 1 part by weight of sodium bicarbonate. Preferably the carbapenem is in the form of the monosodium salt. The pH which results upon dissolution of this formulation is approximately 6.5. Formulating the drug in this manner can extend the stability of the product in solution.

Another formulation that is of particular interest is comprised of about 4–10 parts by weight, and preferably about 6.7 parts by weight, of the compound of formula I, or the pharmaceutically acceptable salt, stabilized form, prodrug or hydrate thereof, and 1 part by weight sodium carbonate. Preferably the carbapenem is in the form of the monosodium salt. The pH which results upon dissolution of this formulation is approximately 7.5. Formulating the drug in this manner can extend the stability of the product in solution.

As mentioned above, the compound of formula I or II can be used in lyophilized or non-lyophilized form. The lyophilized form is produced using standard lyophilization techniques.

Additional components can be included in the compositions of the present invention as well. Since the composition is preferably administered by injection, various diluents, buffers, preservatives, local anesthetics, tonicity controlling agents and other components can be included.

Representative examples of diluents include sterile water for injection, normal saline, dextrose solution 5% (D5W), lactated Ringer's solution and the like. Preferably the diluent is normal saline or sterile water for injection.

Representative examples of buffers include phosphate buffer, such as dihydrogen sodium phosphate, citrate buffer, such as sodium citrate, meglumine and tri(hydroxymethyl) aminomethane.

Representative examples of preservatives include butylhydroxyacetone (BHA), butylhydroxytoluene (BHT) and benzalkonium chloride.

Representative examples of local anesthetics include benzocaine, lidocaine, novacaine, pontocaine and the like.

Representative examples of tonicity modifying agents include sodium chloride, mannitol, dextrose, glucose, lactose and sucrose.

Representative examples of pharmaceutical excipients include water, mannitol, sorbitol, dextrose, lactose, glucose, dextran, sucrose, maltose, gelatin, bovine serum albumin (BSA), glycine, mannose, ribose, polyvinylpyrrolidine (PVP), cellulose derivatives, glutamine, inositol, potassium glutamate, erythritol, serine and other amino acids.

When the compound of formula I is formulated in a pharmaceutical composition with a suitable amount of sodium carbonate or sodium bicarbonate, any or all of the species described herein can be contained in the formulation upon dilution or reconstitution. Compound I represents the non-stabilized form of the free acid. Thus, various salt forms of formula I, such as I-a through I-c, are included herein.

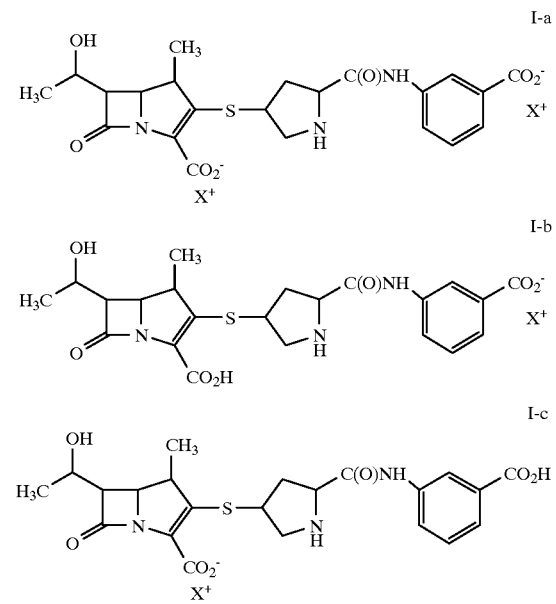

The specie $X^+$ represents a charge balancing cation, which is present in association with the compound as necessary to maintain overall charge neutrality. Typically the charged specie would be a pharmaceutically acceptable salt-forming ion, such as sodium, potassium, magnesium and the like. A divalent specie such as $Ca^{2+}$ can likewise be present, such as when two carboxylate anions are found in the compound, as in formula I-a, or when a half molar quantity is present relative to the compound, such as in formula I-b or I-c. When the counterion includes a bis cationic specie, e.g., $Ca^{+2}$ an appropriate amount is typically present relative to the carbapenem moiety to provide overall charge neutrality. Thus, the half molar equivalent of $Ca^{+2}$ can be included with a mono-carboxylate to maintain overall charge neutrality. All such embodiments are included in the present invention.

Numerous salt-forming ions are recited in Berge, S. M., et al. *J. Pharm. Sci.* 66(1): 1–16 (1977), the teachings of which are incorporated herein by reference.

A preferred group of salt-forming cations represented by $X^+$ is an ion selected from the group consisting of: sodium, potassium, calcium, and magnesium.

More preferably $X^+$ represents a member selected from the group consisting of: $Na^+$, $Ca^{+2}$ and $K^+$.

By including a suitable amount of the carbon dioxide producing compound, preferably sodium bicarbonate or sodium carbonate, one or more of the following stabilized structures is formed

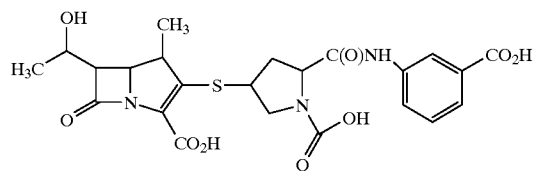

II

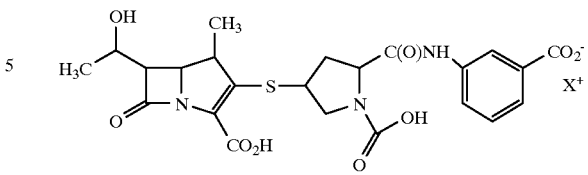

II-g

Compound II above is referred to as the free acid form of the stabilized compound. Compounds II-a through II-g are examples of salt forms of the stabilized compound.

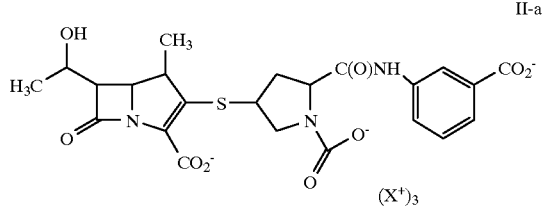

II-a

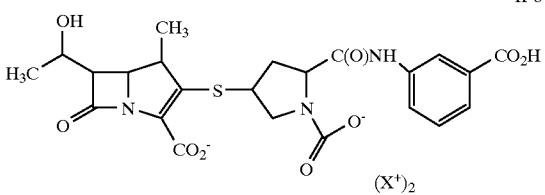

II-b

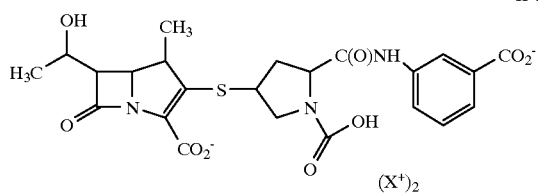

II-c

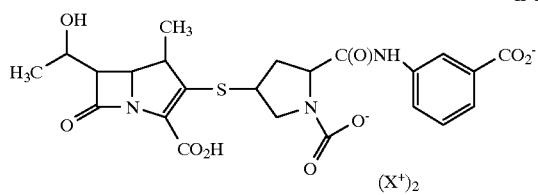

II-d

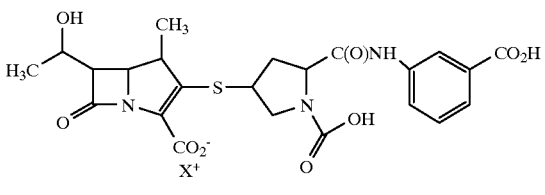

II-e

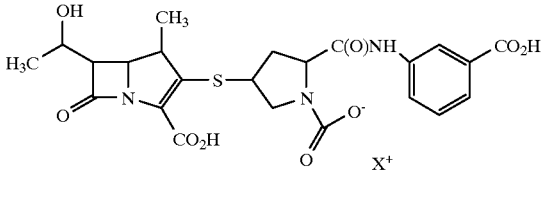

II-f

The amount of the carbon dioxide producing compound, e.g., sodium bicarbonate or sodium carbonate which is included in the composition is that which is sufficient to form compounds of formula II through II-g, and which optionally provides the desired pH of the composition upon dissolution or reconstitution.

To provide electronic balance and overall charge neutrality, from zero to three positively charged counterions are present. Different counterions can be included in the composition. Hence, for example, calcium and sodium could be included together in the pharmaceutical composition to provide overall charge neutrality. The counterions can thus be varied within wide limits. Generally the counterion or counterions are pharmaceutically acceptable cationic species.

The carbapenem compound of the present invention is useful for the treatment of bacterial infections in animal and human subjects. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is concerned with pharmaceutical compositions and methods of treating bacterial infections utilizing the carbapenem compound.

The carbapenem may be used in a variety of pharmaceutical preparations. Compositions for injection, the preferred route of delivery, may be prepared in unit dosage form or in multidose containers. The compositions may take such forms as suspensions, solutions or emulsions, oily or aqueous in nature, and may contain various formulating agents, such as diluents, buffers, preservatives and the like. Hence, the compound is present in combination with these pharmaceutically acceptable carriers.

Alternatively, the active ingredient may be in the form of a powder, which can be reconstituted with a liquid such as sterile water, normal saline and the like at the time of administration. The powder can be in lyophilized or non-lyophilized form.

Representative oral compositions are typically in the form of tablets, capsules, solutions or suspensions. Such compositions may likewise be packaged in unit dose or multidose containers. In these oral compositions, the pharmaceutically acceptable carriers may be comprised of diluents, tabletting and granulating aids, lubricants, disintegrants, buffers, sweeteners, preservatives and the like.

Topical compositions may be formulated with pharmaceutically acceptable carriers in the form of hydrophobic or hydrophilic ointments, creams, lotions, solutions, paints or powders.

The dosage to be administered depends to a large extent upon the condition and size of the mammalian patient being treated as well as the delivery route and frequency of administration. The parenteral route (by injection) is preferred.

The compositions for human delivery per unit dosage, whether liquid or solid, may contain from about 0.01% to about 99% of active material, the preferred range being from about 10–60%. The composition will generally contain from about 10 mg to about 3000 mg of the active ingredient; however, in general, it is preferable to employ a dosage amount in the range of from about 100 mg to about 1000 mg. In parenteral administration, the unit dosage is usually the compound in a sterile water or saline solution or in the form of a powder intended for dissolution or reconstitution.

The preferred method of administration of the compound of formula I is parenterally by intravenous (i.v.) infusion. Alternatively, the compound may be administered by injection intramuscularly (i.m.).

For adults, a dose of about 5 to about 50 mg of the formula I antibacterial compound per kg of body weight is administered from 1 to 6 times per day. The preferred dosage ranges from about 100 mg to about 1000 mg of the compound given one to four times per day, preferably 1–2 times a day, and most preferably once daily.

More specifically, for mild infections a dose of about 100 mg to about 1000 mg from one to four times daily is preferred, most preferably once daily. For moderate infections, a dose of about 500 mg to about 1000 mg from one to four times daily is preferred. For severe, life-threatening infections, a dose of about 1000–2000 mg one to six times daily is preferred.

For children, a dose of 5–25 mg/kg of body weight given 1 to 4 times per day is preferred; a dose of 10 mg/kg from one to four times daily is preferred.

The compound of formula I is of the broad class known as carbapenems. Naturally occurring carbapenems are susceptible to attack by a renal enzyme known as dehydropeptidase (DHP). This attack or degradation may reduce the efficacy of the carbapenem antibacterial agent. The compound used in the present invention is significantly less subject to such attack, and therefore may not require the use of a DHP inhibitor. However, use of a DHP inhibitor is optional and is contemplated as being included in the present invention. Inhibitors of DHP and heir use with carbapenem antibacterial agents are disclosed in European Patent Applications No. 79102616.4, filed Jul. 24, 1979 (Patent No. 007 614); and No. 82107174.3, filed Aug. 9, 1982 (Publication No. 072 014)].

The compound of the present invention may, where DHP inhibition is desired or necessary, be combined or used with the appropriate DHP inhibitor as described in the aforesaid patents and published application. The cited European Patent Application defines the procedure for determining DHP susceptibility of the present carbapenems and disclose suitable inhibitors, combination compositions and methods of treatment.

A preferred weight ratio of formula I compound: DHP inhibitor in combination compositions is about 1:1. A preferred DHP inhibitor is 7-(L-2-amino-2-carboxyethylthio)-2-(2,2-dimethylcyclo-propanecarboxamide)-2-heptenoic acid, or a salt thereof, also known as cilastatin.

The carbapenem is active against various gram-positive and to a lesser extent gram-negative bacteria, and accordingly finds utility in human and veterinary medicine.

The pharmacokinetic profile for the composition described herein is surprisingly better than that of related compounds.

Representative examples of pharmaceutical compositions containing the compounds described herein are shown below.

| Composition 1 | |
|---|---|
| Compound I | 4.5 g |
| Sodium Bicarbonate | 1.0 g |

Powder blend the ingredients noted above . Compound I is in the form of the monosodium salt. The resulting pH of an aqueous solution (225 mL) is approximately 6.5.

| Composition 2 | |
|---|---|
| Compound I | 6.7 g |
| Sodium Carbonate | 1.0 g |

Powder blend the ingredients noted above. Compound I is in the form of the monosodium salt. The resulting pH of the solution (335 mL) is approximately 7.5.

EXAMPLE

| | |
|---|---|
| Compound I | 45.4 mg/mL (equivalent to 36 mg anhydrous free acid) |
| Sodium Bicarbonate, USP | 8.0 mg/mL |
| Sodium Chloride, USP | 4.0 mg/mL |

Powder blend the ingredients noted above as in Composition 1, and combine with water (q.s. 1.0 mL). The final pH of the solution is shown below.

Solution stability of this intravenous formulation was determined at 25° C. with the following results.

| Conc. (mg/mL) | initial pH | final pH | % Remaining in Solution at: | | | | | $k(hr^{-1})$ | t 90% (hrs) |
|---|---|---|---|---|---|---|---|---|---|
| | | | 1 hr | 2 hrs | 4 hrs | 6 hrs | 8 hrs | | |
| 36 mg/mL | 6.7 | 7.3 | 96.7 | 95.7 | 94.1 | 91.8 | 89.9 | 0.010438 | 7.3 |
| *12 mg/mL | 7.0 | 7.4 | 98.6 | 98.0 | 97.2 | 96.5 | 95.0 | 0.004994 | 21.0 |

While certain preferred embodiments of the invention have been described herein in detail, numerous alternative embodiments are contemplated as falling within the scope of the appended claims. Consequently the invention is not to be limited thereby.

What is claimed is:

1. A compound represented by the formula II:

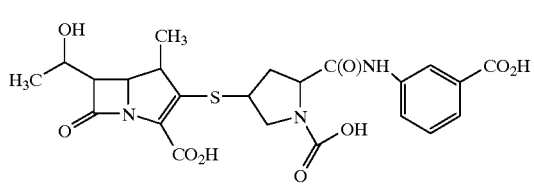

II or a pharmaceutically acceptable salt, prodrug or hydrate thereof.

2. A pharmaceutical composition which is comprised of a compound represented by formula II:

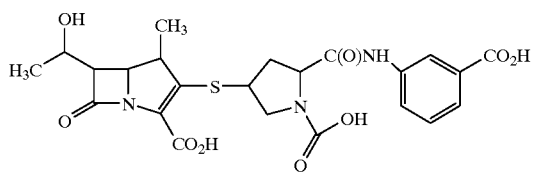

II or a pharmaceutically acceptable salt, prodrug or hydrate thereof, in combination with a pharmaceutically acceptable carrier.

3. A compound in accordance with claim 1 wherein the pharmaceutically acceptable salt is selected from the group consisting of:

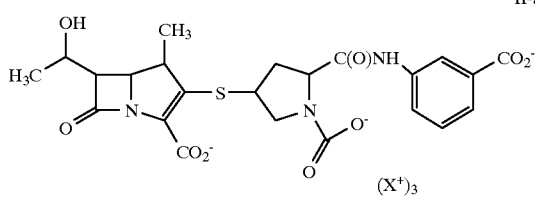

II-a

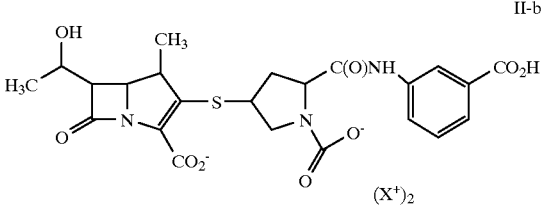

II-b

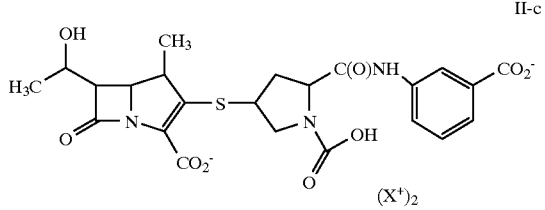

II-c

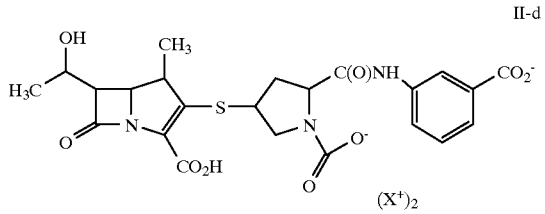

II-d

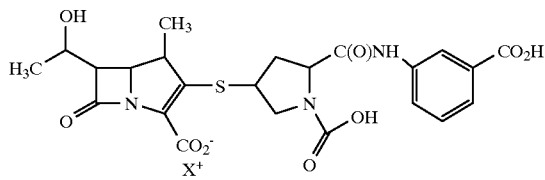

II-e

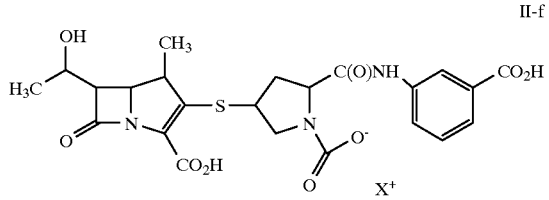

II-f

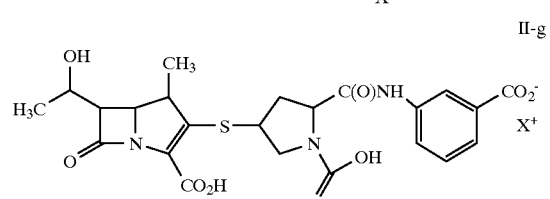

II-g wherein $X^+$ represents a pharmaceutically acceptable cationic group.

4. A method of stabilizing a carbapenem of the formula I:

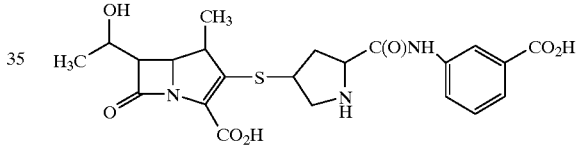

I or a pharmaceutically acceptable salt, prodrug or hydrate thereof, comprising adding to the compound a sufficient amount of a carbon dioxide source to form a compound of formula II:

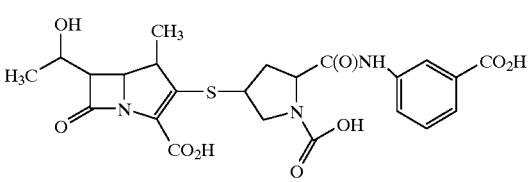

II or a pharmaceutically acceptable salt, prodrug or hydrate thereof.

5. A method in accordance with claim 4 wherein the carbon dioxide source is selected from carbon dioxide, sodium carbonate and sodium bicarbonate.

6. A method in accordance with claim 5 wherein the carbon dioxide source is selected from sodium carbonate and sodium bicarbonate.

* * * * *

UNITED STATES PATENT AND TRADEMARK OFFICE
CERTIFICATE OF CORRECTION

Page 1 of 1

PATENT NO. : 5,952,323
APPLICATION NO. : 09/064426
DATED : September 14, 1999
INVENTOR(S) : Jeffrey A. Zimmerman et al.

It is certified that error appears in the above-identified patent and that said Letters Patent is hereby corrected as shown below:

Title page, item [62], "Division of application No. 08/856,560, May 15, 1997, abandoned" should read -- Division of application No. 08/856,560, filed on May 15,1997, now abandoned, which claims the benefit of U.S. Provisional Application No. 60/018,518, filed on May 28, 1996 --.

In the Specification

Column 1, lines 3-5, "This application is a division of application Ser. No. 08/856,560 filed May 15, 1997. Now abandoned." should read -- This application is a division of application Ser. No. 08/856,560 filed on May 15, 1997, now abandoned, which claims the benefit of U.S. Provisional Application Ser. No. 60/018,518, filed on May 28, 1996. --.

Signed and Sealed this
Twenty-ninth Day of September, 2015

Michelle K. Lee
*Director of the United States Patent and Trademark Office*